(12) United States Patent
Bowe (10) Patent No.: US 7,013,170 B2
(45) Date of Patent: Mar. 14, 2006

(54) METHODS OF CATHETERIZATION USING A DUAL STEER PRESHAPED CATHETER

(75) Inventor: Wade Bowe, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/027,427

(22) Filed: Dec. 30, 2004

(65) Prior Publication Data

US 2005/0107678 A1 May 19, 2005

Related U.S. Application Data

(62) Division of application No. 10/351,847, filed on Jan. 27, 2003.

(51) Int. Cl.
*A61B 5/04* (2006.01)
*A61B 18/14* (2006.01)
*A61N 1/05* (2006.01)

(52) U.S. Cl. .......................... 600/374; 606/41; 607/122
(58) Field of Classification Search ................ 600/374; 606/41; 607/122
See application file for complete search history.

(56) References Cited

U.S. PATENT DOCUMENTS

| 5,383,852 A * | 1/1995 | Stevens-Wright ........ 604/95.04 |
| 5,673,695 A * | 10/1997 | McGee et al. .............. 600/374 |
| 6,096,036 A | 8/2000 | Bowe et al. |
| 6,572,611 B1 * | 6/2003 | Falwell ........................ 606/41 |

* cited by examiner

*Primary Examiner*—Lee S. Cohen
(74) *Attorney, Agent, or Firm*—Hollingsworth & Funk, LLC (57) ABSTRACT

Methods of manipulating a catheterization apparatus involve providing a catheter having a flexible shaft with a preformed curve on a distal end of the flexible shaft, one or more electrodes disposed along the distal end of the flexible shaft, and a shape deflection area defined as a region on the flexible shaft between the preformed curve and a generally straight proximal portion of the flexible shaft. A first steering mechanism is anchored at a distal portion of the preformed curve, and a second steering mechanism is anchored distal to the shape deflection area. The method also involves changing a curvature of the preformed curve in response to a proximally directed force applied to the first steering mechanism, and moving the distal end of the catheter relative to the proximal portion of the flexible shaft in response to a proximally directed force applied to the second steering mechanism.

20 Claims, 5 Drawing Sheets

METHODS OF CATHETERIZATION USING A DUAL STEER PRESHAPED CATHETER

RELATED PATENT DOCUMENTS

This is a divisional of U.S. patent application Ser. No. 10/351,847, filed on Jan. 27, 2003, to which Applicant claims priority under 35 U.S.C. §120, and which is incorporated herein by reference.

FIELD OF THE INVENTION

The invention relates generally to catheter systems and catheterization methods, and, more particularly, to methods involving pre-shaped electrophysiology catheters useful for treating heart conditions.

BACKGROUND OF THE INVENTION

Electrophysiological (EP) treatments are procedures used for dealing with heart arrhythmias and related heart diseases. In general, EP heart treatments involve introducing one or more electrodes into the heart where a diagnostic or therapeutic procedure can be carried out. The electrodes are sometimes attached to the tip of an EP catheter. The EP catheter can be used for procedures such as mapping of electrical activity and ablation, the latter procedure using powerful electrodes to destroy small areas of tissue that cause arrhythmia or other heart disorders.

Maneuvering EP catheters into heart chambers can be complicated. The path that must be traversed is often complex. The catheters must be flexible enough to maneuver through convoluted geometries, yet stiff enough to allow pushing and torquing the catheter from a proximal location. Once an EP catheter is in the general location of therapy, a positive contact must be made between the catheter and target heart tissue. Oftentimes the EP catheter contains a preshaped tip optimized for the intended tissue structure. After positioning the catheter within the target area, the shape of the distal end of an EP catheter may not always be ideally suited to the task. In such an event, the catheter must be removed and a different shaped catheter introduced, costing valuable procedure time.

There is a need for an EP catheter that allows easy maneuvering and in-place alteration of the catheter's distal end. The present invention addresses these needs, as well as other deficiencies of prior art implementations and techniques.

SUMMARY OF THE INVENTION

To overcome the limitations in the prior art described above, and to overcome other limitations that will become apparent upon reading and understanding the present specification, the present invention discloses a pre-shaped steerable catheter that can be used for a variety of purposes, including electrophysiological treatment of cardiac and venous structures.

According to one embodiment of the present invention, a method of manipulating a catheterization apparatus involves providing a catheter. The catheter includes a flexible shaft having a preformed curve on a distal end of the flexible shaft, one or more electrodes disposed along the distal end of the flexible shaft, and a shape deflection area defined as a region on the flexible shaft between the preformed curve and a generally straight proximal portion of the flexible shaft. The catheter further includes a first steering mechanism anchored at a distal portion of the pre-formed curve and a second steering mechanism anchored on the flexible shaft distal to the shape deflection area of the flexible shaft. The method also involves changing a curvature of the preformed curve in response to a proximally directed force applied to the first steering mechanism, and moving the distal end of the catheter relative to the proximal portion of the flexible shaft in response to a proximally directed force applied to the second steering mechanism.

In accordance with another embodiment, a method of manipulating a catheterization apparatus involves introducing a catheter into a heart chamber, the catheter having a construction as described herein. The method involves maneuvering the catheter so that the distal end of the flexible shaft is proximate heart tissue of interest, actuating the first steering apparatus of the catheter to change a curvature of the distal end of the flexible shaft, and actuating the second steering apparatus of the catheter to change an orientation of the distal end of the flexible shaft relative to a proximal portion of the flexible shaft. Actuating one or both of the first and second steering apparatuses causes the distal end of the flexible shaft to conform to at least a portion of the heart tissue of interest.

In a further embodiment, an electrophysiology catheter system includes a flexible shaft having a preformed curve on a distal end. One or more electrodes are disposed along the distal end of the shaft. The shaft includes a shape deflection area defined as a region on the shaft between the preformed curve and a generally straight proximal portion of the shaft. A first anchor member is located at a distal portion of the pre-formed curve and a second anchor member is located distal to the shape deflection area of the flexible shaft.

A first and second steering tendon are coupled to the first and second anchor members, respectively. A force applied to a proximal end of the first steering tendon causes a change in the curvature of the preformed curve. A force applied to the proximal end of the second steering tendon causes a movement of the distal end of the flexible shaft relative to the proximal portion of the flexible shaft.

In another embodiment of the present invention, a method of providing electrophysiological therapy to a heart tissue includes introducing a catheter adapted for electrophysiology into a heart chamber. The catheter is maneuvered so that a distal end of the catheter is proximate the heart tissue. A first steering apparatus of the catheter is activated to change a curvature of the distal end of the catheter. A second steering apparatus of the catheter is activated to change an orientation of the distal end relative to a proximal portion of the catheter. Activating either of the first and second steering apparatus causes the distal end of the catheter to conform to a portion of the heart tissue.

In another embodiment of the present invention, a catheter adapted for electrophysiological therapy includes a flexible shaft with a preformed curve on a distal end of the flexible shaft. An electrical energy delivery means is disposed along the distal end of the flexible shaft. The shaft includes a shape deflection area, defined as a region on the shaft between the preformed curve and a generally straight proximal portion of the flexible shaft.

A first steering means is included for changing a curvature of the preformed curve of the flexible shaft. A second steering means is included for changing a movement of the distal end of the flexible shaft about the shape deflection area without substantially changing the curvature of the pre-formed curve of the flexible shaft.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In broad and general terms, a catheter system of the present invention employs a flexible shaft having a pre-formed bend at a distal end. A plurality of electrodes are deployed along the outer surface of the catheter's distal end. Two steering tendons are deployed in the catheter. One steering tendon changes the shape of the pre-formed distal bend while the other steering tendon moves the distal section relative to the proximal part of the catheter shaft.

A catheter according to the present invention may be adapted for electrophysiology (EP) treatments within the chambers of the heart. It is appreciated, however, that the concepts described herein are applicable to any type of catheter, such as guide catheters and drug delivery catheters. For purposes of illustration, the invention will be described in terms of an EP catheter used by a clinical electrophysiologist when mapping electrical paths and ablating heart tissues to eliminate arrhythmias, and specifically to treat atrial fibrillation.

EP catheters typically fall within two general categories: preshaped catheters and steerable catheters. The contours of preshaped catheters are generally fixed. This is often achieved in production by constraining the catheter's distal end within a shaping fixture and warming the fixture until the catheter assumes the intended shape (i.e. by "heat setting" the polymer shaft). On the other hand, a steerable catheter is generally formed with a straight end, and a curve is induced by applying tension to one or more steering tendons. When steered, the distal ends of such steerable catheters may assume a circular or semi-circular arc having a radius of curvature that depends on the amount of tension applied to the steering tendon(s).

In a catheter according to the present invention, the end of the catheter is preshaped to approximate the anatomical requirement. The catheter's shape can be set by inclusion of a preformed stylet as opposed to heat setting the shaft. Once the preformed portion of the catheter is within the heart chamber, the catheter's shape is adjustable at two points via two internal steering mechanisms. In this way a catheter according to the present invention can include advantages of both preshaped and steered catheters.

Figure 1:
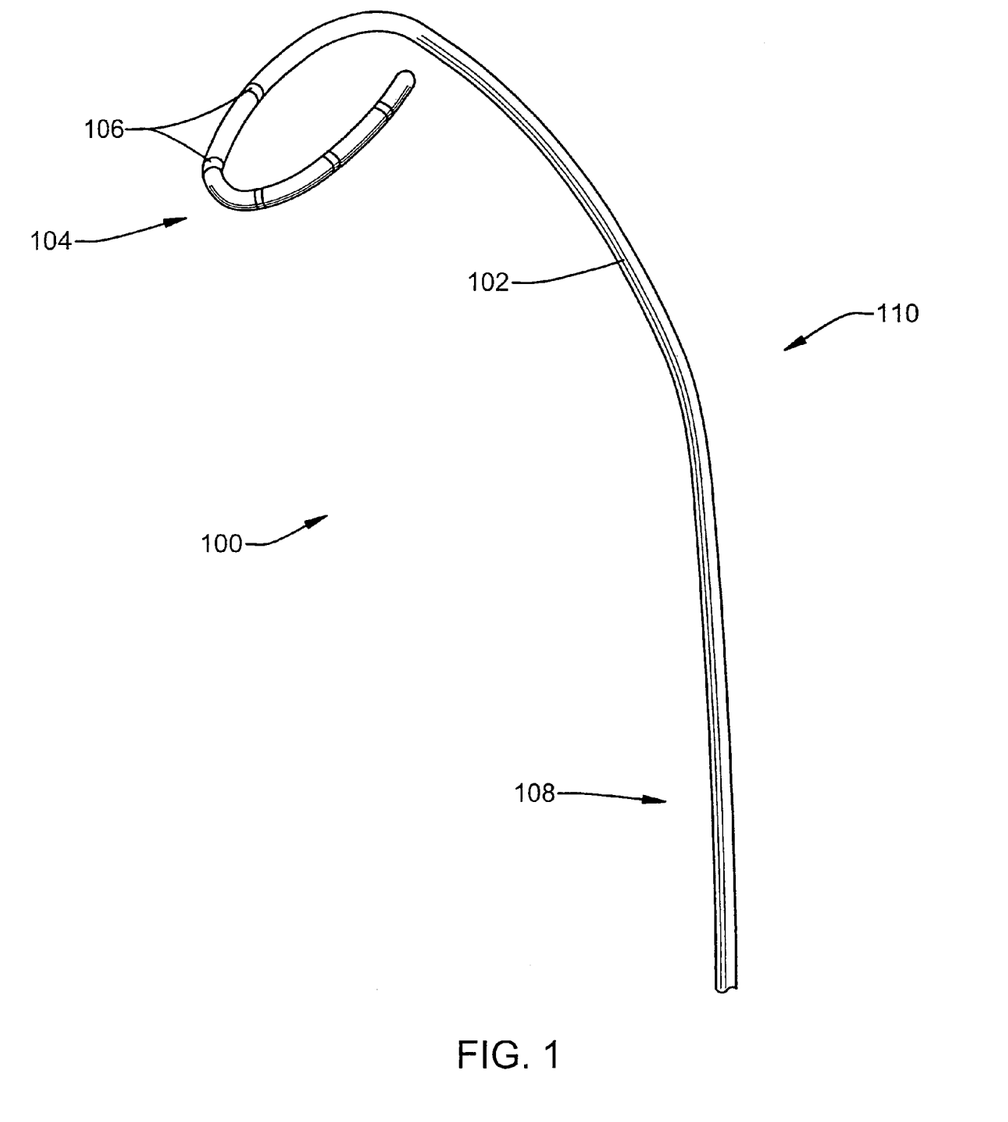
FIG. 1 is a perspective view of the distal end of a catheter according to an embodiment of the present invention.

Turning now to FIG. 1, a distal portion of an EP catheter 100 is shown. The catheter 100 includes a flexible shaft 102 that is suited for maneuvering into anatomical locations such as heart vessels. The shaft 102 is typically formed of a polymeric material and can include reinforcing and stiffening features such as metallic sheathing or braiding.

A distal end 104 of the catheter 100 includes a preformed curve having a shape suitable for treating the area of interest. The distal end 104 illustrated in FIG. 1 is a circular loop suited for ablation of certain blood vessels such as the pulmonary vein. A closed or open loop at the distal end 104 has been found useful for ablation in veins and arteries, although it is appreciated any curved shape can be used on the distal end 104 depending on the application and anatomical region targeted for treatment.

One or more electrodes 106 may be deployed on the distal end 104 of the catheter 100. Electrodes for ablation/EP can be formed as band electrodes for catheter mounting and are sometimes made from platinum/iridium. However, the electrodes 106 may be fabricated from any suitable materials, such as stainless steel for electrocardiagram measurements. Other measurement devices may also be employed on the distal end 104 with the electrodes 106. Devices such as thermal sensors (not shown) can be used when performing ablation to ensure lesions are effectively formed by the electrodes.

The curvature of the distal end 104 of the catheter 100 can be made variable by including various steering apparatus (not shown) within the flexible shaft. The flexible shaft 102 is generally straight at a proximal portion 108. Between the proximal portion 108 and the distal end 104 a predetermined deflection area 110 is defined. The distal end 104 can be made to deflect about the deflection area 110 by use of a second steering apparatus (not shown).

In practice, the location of the deflection area 110 may vary slightly, given that bending may occur over differing portions of the shaft 102 under differing conditions (e.g. temperature, local support structures, multiple steering apparatus, etc.). Regardless, it is appreciated that a steering apparatus can be devised to restrict bending to a predictable deflection area 110 under most conditions. By deflecting the shaft 102 about the deflection area 110, the relative orientation of the distal end 104 can be varied without affecting the shape of the distal end 104.

Figure 2:
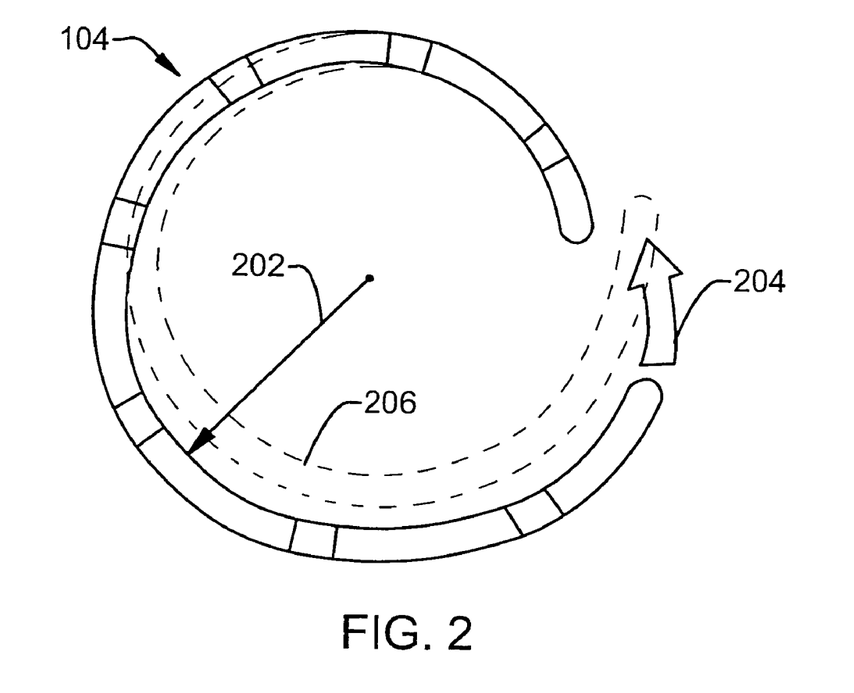
FIG. 2 is a side view of the distal end of the catheter showing a steering mode that changes a distal end curvature according to the concepts of the present invention.
Figure 3:
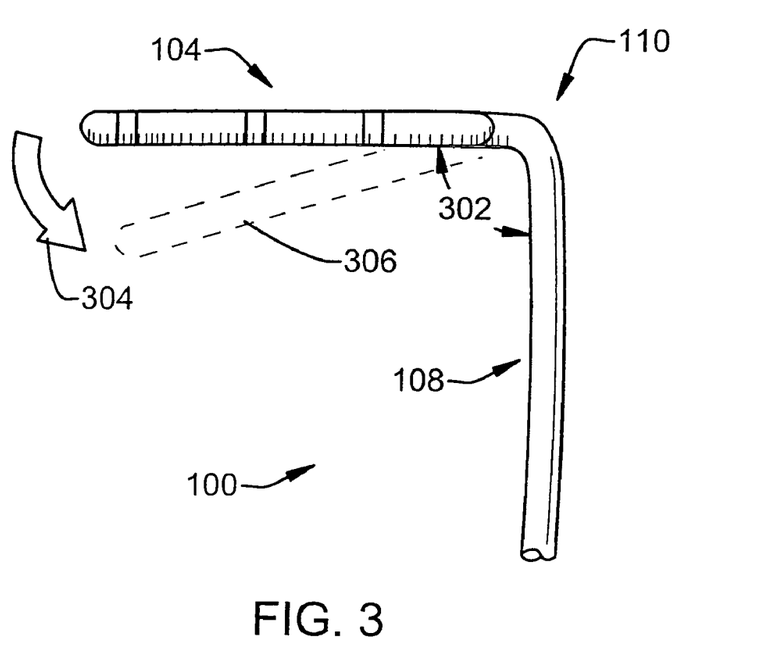
FIG. 3 is a top view of the distal end of the catheter showing another steering mode of the catheter's distal end according to concepts of the present invention.

FIGS. 2 and 3 illustrate the deflection of the catheter's distal end 104 by steering apparatus. FIG. 2 is a top view of the catheter 100 (the designation of a "top" view is arbitrary and assumes the proximal potion 108 of the shaft is oriented vertically as seen in FIG. 3). The distal end 104 has a radius of curvature 202 that can be increased or decreased by a steering apparatus. The arrow 204 indicates the general direction of movement near the distal tip when the radius of curvature 202 is decreased. When decreasing the radius of curvature 202, the distal end 104 assumes a deflected orientation 206 as shown in dashed lines. When a steering mechanism increases the radius of curvature 202, the opposite deflection is seen (i.e. the loop widens).

FIG. 3 is a side view of the catheter 100 in an orientation similar to that of FIG. 2. The distal end 104 forms an angle 302 with the proximal portion 108 of the catheter 100. A steering apparatus can be used to rotate the distal end 104 about the deflection area 110 thereby increasing or decreasing the angle 302. Decreasing the angle 302 causes the distal end 104 to deflect in a direction generally indicated by the arrow 304. The deflected orientation 306 caused by decreasing the angle 302 is shown in dashed lines. Note that the curvature of the distal end 104 can remain substantially unchanged while changing the angle 302.

Figure 4:
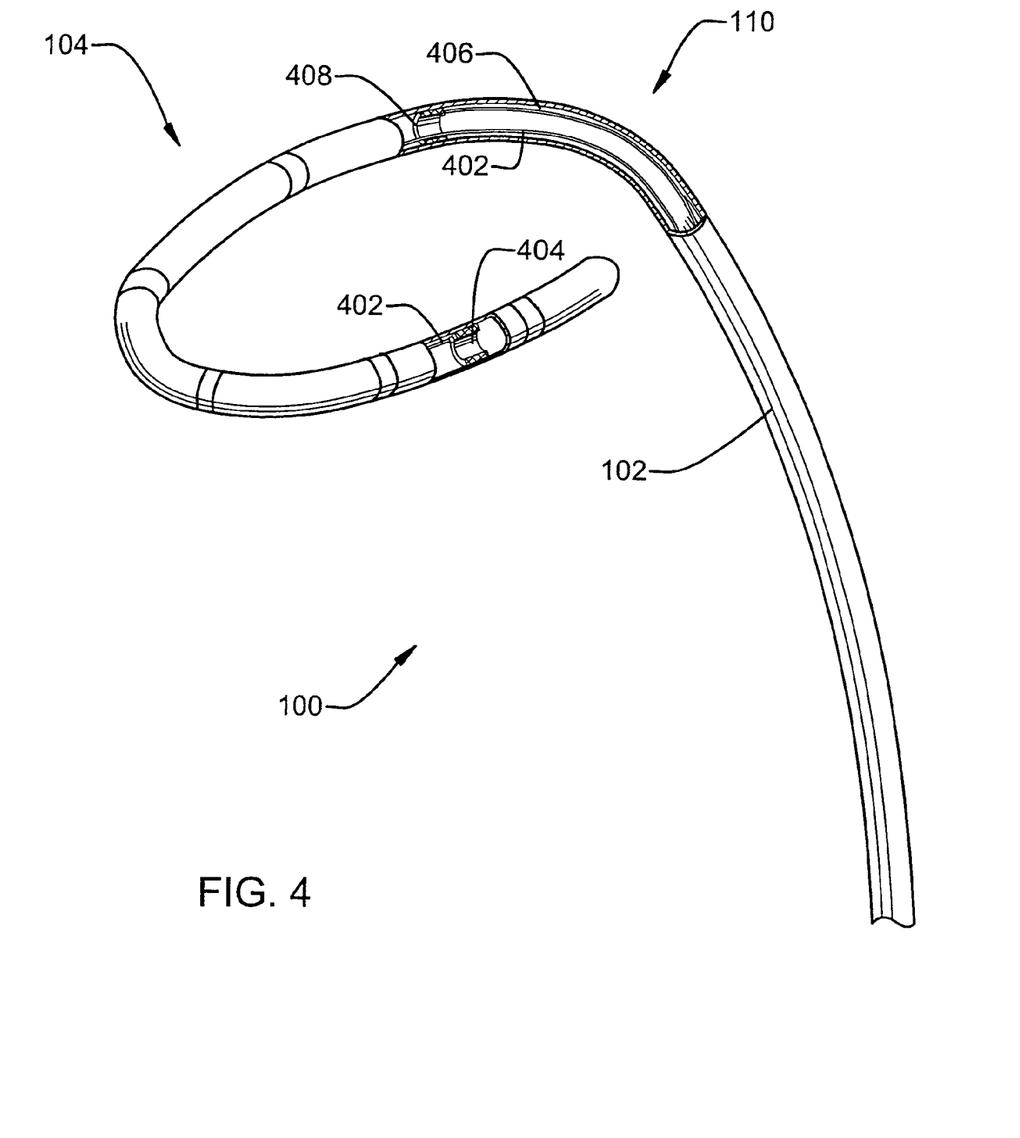
FIG. 4 is a perspective cutaway view of the distal end of the catheter showing steering tendons and anchor members according to an embodiment of the present invention.

Turning now to FIG. 4, an example arrangement of a steering apparatus is shown. A first steering tendon 402 is attached to a first anchor member 404 located at a distal portion of the pre-formed distal end 104. A second steering tendon 406 is attached to a second anchor member 408 located distal to the deflection area 110.

The anchor members 404, 408 can be constructed using various materials and construction methods known in the art, including simply bonding a distal part of the tendon to the shaft. In the illustrated configuration, the anchor members 404, 408 are formed of stainless steel rings to which steering tendons 402, 406, respectively, can be welded or soldered. The steering tendons 402, 406 may also be attached to the anchor members 404, 408 using a mechanical interference fit such as a crimp or a stop member. The steering tendons 402, 406 are typically made of metallic (e.g. stainless steel) members such as solid wire, braided wire, or ribbon material. It is possible to form tendons 403, 406 from non-metallic members such as high strength composite members (e.g. Kevlar, carbon fiber).

The anchor members 404, 408 may be embedded within the walls of the shaft 102 during shaft construction. Alternatively, the anchor members 404, 408 may be adhered to the inner wall of the shaft 102 by adhesive bonding or hot melting the shaft material. Hot melting may be performed by heating the anchor members 404, 408 while in intimate contact with the inner walls of the shaft 102. Another method of attaching the anchor members 404, 408 involves butting the bands against a support structure of the shaft 102 such as a reinforcement cage or braid.

Figure 5:
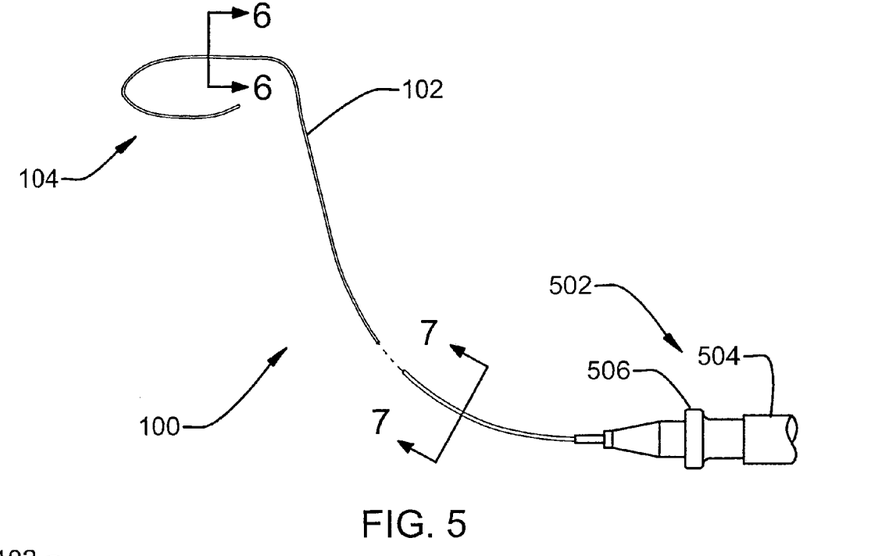
FIG. 5 is a side view of a catheter according to an embodiment of the present invention.
Figure 6:
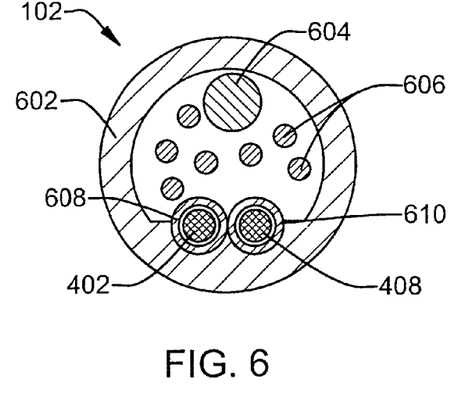
FIG. 6 is a cross sectional view of a distal part of the catheter shaft corresponding to section 6—6 in FIG. 5.
Figure 7:
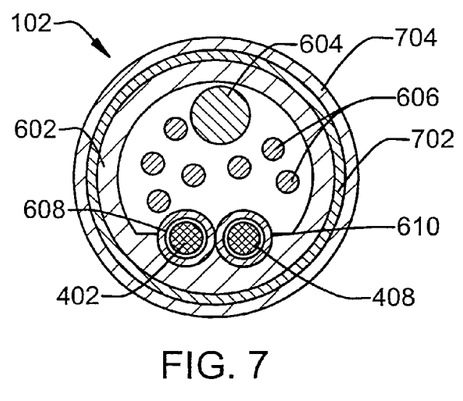
FIG. 7 is a cross sectional view of a proximal part of the catheter shaft corresponding to section 7—7 in FIG. 5.

FIGS. 5–7 illustrate further details of a catheter according to one embodiment of the present invention. FIG. 5 is an external view of the catheter 100 including a proximal handle assembly 502. The proximal handle assembly 502 typically includes a grip 504 and a steering member 506. The handle assembly 502 can be constructed by principles known in the art, such as described in U.S. Pat. Nos. 6,096,036 and 6,270,496, which are hereby incorporated by reference in their respective entireties.

FIG. 6 is a cross section of a distal part of the catheter shaft 102 roughly corresponding to section 6—6 in FIG. 5. The shaft 102 includes a wall 602 formed of polymer, typically a high durometer Pebax material. For cardiac applications, the outer surface of the shaft wall 602 typically has an approximate outer diameter of 2.4 mm (7F).

The shaft wall 602 encloses a stylet 604. The stylet 604 is typically made of a resilient, shape-memory member such as a wire formed of nitinol wire or other superelastic alloy. A nitinol stylet 604 is preshaped by heating the stylet 604 while it is being constrained in the desired shape. A stylet 604 formed in this way is then inserted into the shaft 102 to impart the preformed shaped at the distal end 104 of the shaft 102. The stylet 604 is typically affixed at or near the tip of the shaft 102 to prevent migration of the stylet 604 within the catheter 100 during use.

The outer wall 602 of the shaft 102 also encloses conductors 606 coupled to the tip electrodes 106 (see FIG. 1). The conductors 606 may provide power to the electrodes 106 in ablative applications, and/or provide signals from the electrodes 106 in EP mapping applications. Also shown within the shaft 102 are the steering tendons 402, 408. The steering tendons 402, 408 are disposed within lumens 608, 610, respectively. The lumens 608, 610 are typically formed of a lubricous material such as PTFE and may be affixed to an inner surface of the shaft wall 602.

FIG. 7 shows a cross section of a proximal part of the catheter shaft 102. The layout of the shaft 102 is similar to that seen in FIG. 6, and additionally shows a reinforcing member 702 and an outer casing 704. The reinforcing member can include a braid, cage, ribbon, or other reinforcing member that provides axial and torsional stiffness to the shaft 102 while still allowing a reasonable amount of bending in the shaft 102. The outer casing 704 may be made of a Pebax material having a similar durometer as the shaft wall 602, or may be made of a different material having unique protective and/or lubricous properties.

The differences between the distal and proximal cross sections (e.g. inclusion of a proximal support member 702) as seen in FIGS. 6 and 7 result in the proximal portion having greater stiffness than the distal portion. Other variations in stiffness may also be advantageously induced along portions of the flexible shaft 102. To vary stiffness of the shaft 102, the bending properties of the shaft wall 602 may be changed (e.g. the durometer of the polymeric materials) or the stylet characteristics (e.g. outer diameter or cross section) can be varied along the shaft length. Varying the stiffness along the length of the shaft 102 can beneficially enhance the deflectability of the steered sections or to tune the stiffness of the distal end 104 to minimize the risk of trauma.

Figure 8:
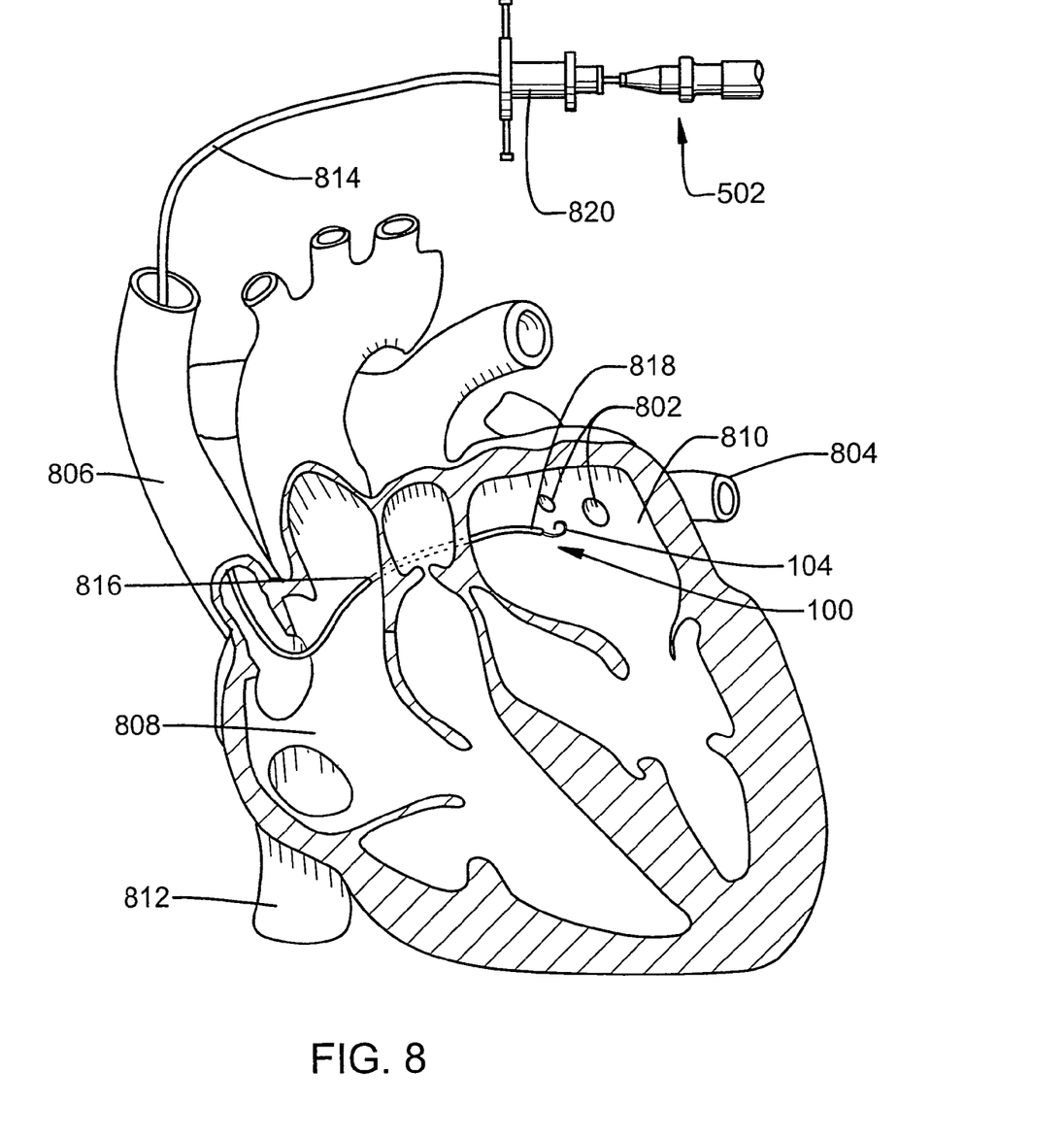
FIG. 8 is a cutaway view of a heart showing a catheter being used according to concepts of the present invention.

FIG. 8 illustrates one particular use of a catheter 100 according to concepts of the present invention. In this example, the catheter 100 is configured for EP mapping and/or ablation and is situated near the ostium(s) 802 of one or more pulmonary veins 804. The distal end 104 of the catheter 100 can be used to measure electrical impulses from heart tissue as well as delivering electrical energy (ablation) to the treatment area of the heart. Ablation results in a lesion that will block any impulses firing from around the treatment area, thus preventing atrial fibrillation from occurring.

A seen in FIG. 8, a distal end 104 shaped as a circular loop can be used to create circular continuous lesions for treatment of atrial fibrillation or atrial flutter. The ostiums 802 of the pulmonary veins 804 are common treatment areas for atrial fibrillation. Less common treatment areas include the superior vena cava 806, right atrium 808, left atrium 810, and the coronary sinus (not shown).

One procedure used in placing the catheter 100 into a heart chamber involves percutaneously introducing the catheter 100 through a large blood vessel. The catheter 100 is then guided through this vessel into the right atrium 808. Various routes to the right atrium can be used through upper blood vessels such as the right internal jugular vein, and right or left subclavian vein. Lower blood vessels, such as the femoral veins, can also be used to enter the right atrium through the inferior vena cava 812. A guide member 814 is typically introduced through one of these paths into the right atrium 808 and then to the left atrium 810 using a transseptal puncture 816. The guide member is typically an introducer sheath or guide catheter. In FIG. 1, an upper blood vessel route is illustrated, with the guide member 814 entering the right atrium 808 through the superior vena cava 806.

A guide member 814 typically includes a large lumen of sufficient size to allow the EP catheter 100 to pass through. A guide member 814 may include a catheter with steering features that allow maneuvering the catheter's distal end 818 from a proximal handle 820. Visualization techniques such as fluoroscopy or ultrasound may assist the clinician in moving the guide member 814 into the correct position.

Once the guide member 814 has cannulated the heart vessels of interest, the EP catheter 100 is advanced along the guide member 814. When the guide member 814 is a catheter, the EP catheter is fed through a guide lumen. The resilient distal end 104 of the EP catheter 100 will generally straighten out while being fed through a guide lumen. Once the tip of the EP catheter 100 emerges from the distal end 818 of the guide member 814, the distal end 104 of the EP catheter 100 will resume its preformed shape.

The first steering tendon 402 (see FIG. 4) allows adjustment of the curve at the EP catheter's distal end 104 to account for variability of heart structures such as the pulmonary vein ostium 802. Adjustment of the first steering tendon 402 allows the clinician to achieve positive contact between the distal end 104 and the ostium 802, thereby ensuring a more successful ablation.

The second steering tendon 406 (see FIG. 4) allows varying the general orientation of the distal end 104 while maneuvering the catheter 100 to the destination vessels. The second steering tendon 406 thereby allows quicker positioning of the distal end 104 as well as allowing better electrode to tissue contact, especially when used in concert with the first steering tendon 402.

It is also appreciated that a steering feature on the guide member 814 (e.g. a steerable guide catheter) can further assist in positioning the distal end 104 of the EP catheter 100. The steering features of the EP catheter 100 and the guide member 814 in conjunction with visual feedback (e.g. fluoroscopy) allows a clinician to quickly and readily manipulate an EP catheter 100 into position.

Although a guide member 814 that includes a catheter or similar sheath apparatus is commonly used, it is appreciated that other guide members may be used in accordance with principles of the present invention. An EP catheter 100 may include an open lumen so that the catheter can be introduced over a guide wire or small catheter. Alternatively, the EP catheter 100 may be introduced without any guide apparatus.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of manipulating a catheterization apparatus, comprising:
   providing a catheter comprising a flexible shaft having a preformed curve on a distal end of the flexible shaft, one or more electrodes disposed along the distal end of the flexible shaft, and a shape deflection area defined as a region on the flexible shaft between the preformed curve and a generally straight proximal portion of the flexible shaft, the catheter further comprising a first steering mechanism anchored at a distal portion of the pre-formed curve and a second steering mechanism anchored on the flexible shaft distal to the shape deflection area of the flexible shaft;
   changing a curvature of the preformed curve in response to a proximally directed force applied to the first steering mechanism; and
   moving the distal end of the catheter relative to the proximal portion of the flexible shaft in response to a proximally directed force applied to the second steering mechanism.

2. The method of claim 1, wherein moving the distal end of the catheter comprises changing a movement of the distal end of the distal end of the flexible shaft about the shape deflection area without substantially changing the curvature of the preformed curve of the flexible shaft.

3. The method of claim 1, further comprising delivering energy from the one or more electrodes sufficient to ablate cardiac tissue.

4. The method of claim 1, further comprising sensing signals indicative of cardiac activity using the one or more electrodes.

5. The method of claim 1, further comprising mapping a cardiac structure using sense signals received from the one or more electrodes.

6. The method of claim 1, further comprising providing a stylet within the distal end of the flexible shaft, and shaping the preformed curve on the flexible shaft using the stylet.

7. The method of claim 6, wherein the stylet comprises a resilient and shape retentive member.

8. The catheter of claim 6, wherein the stylet comprises a nitinol wire.

9. The method of claim 1, wherein the preformed curve comprises a substantially circular loop.

10. The method of claim 1, wherein the one or more electrodes comprise a plurality of band electrodes.

11. A method of manipulating a catheterization apparatus, comprising:
    introducing a catheter into a heart chamber, the catheter comprising a flexible shaft having a preformed curve on a distal end of the flexible shaft, one or more electrodes disposed along the distal end of the flexible shaft, and a shape deflection area defined as a region on the flexible shaft between the preformed curve and a generally straight proximal portion of the flexible shaft, the catheter further comprising a first steering apparatus anchored at a distal portion of the pre-formed curve and a second steering apparatus anchored on the flexible shaft distal to the shape deflection area of the flexible shaft;
    maneuvering the catheter so that the distal end of the flexible shaft is proximate heart tissue of interest;
    actuating the first steering apparatus of the catheter to change a curvature of the distal end of the flexible shaft; and
    actuating the second steering apparatus of the catheter to change an orientation of the distal end of the flexible shaft relative to a proximal portion of the flexible shaft;

wherein actuating one or both of the first and second steering apparatuses causes the distal end of the flexible shaft to conform to at least a portion of the heart tissue of interest.

12. The method of claim 11, wherein actuating the second steering apparatus results in changing movement of the distal end of the distal end of the flexible shaft about the shape deflection area without substantially changing the curvature of the preformed curve of the flexible shaft.

13. The method of claim 11, further comprising delivering energy from the one or more electrodes sufficient to ablate cardiac tissue.

14. The method of claim 11, further comprising mapping at least the cardiac tissue of interest using sense signals received from the one or more electrodes.

15. The method of claim 11, further comprising providing a stylet within the distal end of the flexible shaft, and shaping the preformed curve on the flexible shaft using the stylet.

16. The method of claim 15, wherein the stylet comprises a resilient and shape retentive member.

17. The method of claim 11, wherein the preformed curve comprises a substantially circular loop.

18. The method of claim 11, wherein the one or more electrodes comprise a plurality of band electrodes.

19. The method of claim 11, wherein introducing the catheter comprises introducing a guide member into the heart chamber and advancing the catheter along the guide member.

20. The method of claim 19, wherein the guide member comprises a guide catheter, and introducing the guide catheter into the heart chamber comprises activating a steering apparatus of the guide catheter to steer a distal tip of the guide catheter.

* * * * *